(12) United States Patent
DiCesare et al.

(10) Patent No.: US 10,058,689 B2
(45) Date of Patent: Aug. 28, 2018

(54) IMPLANTABLE DRUG DELIVERY DEVICES FOR GENITOURINARY SITES

(71) Applicant: TARIS BIOMEDICAL LLC, Lexington, MA (US)

(72) Inventors: Paul DiCesare, Easton, CT (US); Jeffrey Radziunas, Wallingford, CT (US); Andrew Barnes, Naugatuck, CT (US); Eric Britschock, Willington, CT (US); David Sutton, Shelton, CT (US)

(73) Assignee: TARIS Biomedical LLC, Lexington, MA (US)

( * ) Notice: Subject to any disclaimer, the term of this patent is extended or adjusted under 35 U.S.C. 154(b) by 136 days.

(21) Appl. No.: 15/056,097

(22) Filed: Feb. 29, 2016

(65) Prior Publication Data

US 2016/0213904 A1    Jul. 28, 2016

Related U.S. Application Data

(63) Continuation of application No. 13/813,745, filed as application No. PCT/US2011/046439 on Aug. 3, 2011, now Pat. No. 9,283,361.
(Continued)

(51) Int. Cl.
*A61M 31/00* (2006.01)

(52) U.S. Cl.
CPC .................. *A61M 31/002* (2013.01)

(58) Field of Classification Search
CPC ...... A61M 2205/04; A61M 2210/1085; A61M 31/002; A61M 2210/1078; A61F 2250/0068
See application file for complete search history.

(56) References Cited

U.S. PATENT DOCUMENTS

| | | | |
|---|---|---|---|
| 3,901,232 A | | 8/1975 | Michaels et al. |
| 3,995,633 A | * | 12/1976 | Gougeon ............... A61F 6/08 128/832 |

(Continued)

FOREIGN PATENT DOCUMENTS

| | | |
|---|---|---|
| DE | 3332156 A1 | 3/1985 |
| EP | 0572932 A2 | 12/1993 |

(Continued)

OTHER PUBLICATIONS

Giannantoni, et al., "New Frontiers in Intravesical Therapies and Drug Delivery," European Urology, vol. 50 (2006), pp. 1183-1193, Elsevier B.V.

(Continued)

*Primary Examiner* — Rebecca E Eisenberg
(74) *Attorney, Agent, or Firm* — Eversheds Sutherland (US) L LP

(57) ABSTRACT

Implantable drug delivery devices are provided to have a deployment shape for implantation in the body and a retention shape for retention in the body. The device may have one or more elongated drug reservoirs containing a drug, and the drug reservoir may be formed from a deformable material. In one case, a first filament is attached to the first end of the drug reservoir and second filament is attached to the second end of the drug reservoir, wherein a fastener is positioned about the first and second filaments to permit shortening and prevent lengthening of the filaments with reference to the ends of the drug reservoir, as a means for transforming the device from the implantation shape to the retention shape.

16 Claims, 15 Drawing Sheets

Related U.S. Application Data

(60) Provisional application No. 61/370,902, filed on Aug. 5, 2010.

(56) References Cited

U.S. PATENT DOCUMENTS

| | | | |
|---|---|---|---|
| 4,016,251 A | 4/1977 | Higuchi et al. | |
| 4,475,916 A | 10/1984 | Himmelstein | |
| 4,871,542 A | 10/1989 | Vilhardt | |
| 5,062,829 A * | 11/1991 | Pryor | A61D 7/00 424/438 |
| 5,334,189 A * | 8/1994 | Wade | A61M 31/002 422/68.1 |
| 6,039,967 A | 3/2000 | Ottoboni et al. | |
| 6,086,909 A | 7/2000 | Harrison et al. | |
| 6,171,298 B1 | 1/2001 | Matsuura et al. | |
| 6,296,622 B1 | 10/2001 | Kurz et al. | |
| 6,524,608 B2 | 2/2003 | Ottoboni et al. | |
| 6,537,193 B1 | 3/2003 | Lee et al. | |
| 7,232,421 B1 | 6/2007 | Gambale et al. | |
| 8,182,464 B2 * | 5/2012 | Lee | A61K 9/0034 424/703 |
| 2003/0073979 A1 | 4/2003 | Naimark et al. | |
| 2004/0260027 A1 | 12/2004 | Friedman et al. | |
| 2005/0234013 A1 | 10/2005 | Parsons | |
| 2005/0238733 A1 | 10/2005 | Henry | |
| 2006/0105010 A1 | 5/2006 | Rahe et al. | |
| 2006/0264912 A1 | 11/2006 | Mcintyre et al. | |
| 2007/0172508 A1 | 7/2007 | Zupkas et al. | |
| 2007/0202151 A1 | 8/2007 | Lee et al. | |
| 2009/0062825 A1 | 3/2009 | Pool et al. | |
| 2009/0149833 A1 | 6/2009 | Cima et al. | |
| 2009/0182404 A1 | 7/2009 | Shokoohi | |
| 2010/0003297 A1 | 1/2010 | Tobias et al. | |
| 2010/0023056 A1 | 1/2010 | Johansson et al. | |
| 2010/0076261 A1 | 3/2010 | Neeman et al. | |
| 2010/0330149 A1 | 12/2010 | Lee et al. | |
| 2011/0060309 A1 | 3/2011 | Lee et al. | |

FOREIGN PATENT DOCUMENTS

| | | |
|---|---|---|
| WO | 98/31415 A1 | 2/1998 |
| WO | 99/18884 A1 | 4/1999 |
| WO | 00/040234 A1 | 7/2000 |
| WO | 01/067991 A1 | 9/2001 |
| WO | 02/085428 A2 | 10/2002 |
| WO | 03/009882 A2 | 2/2003 |
| WO | 04/037318 A2 | 5/2004 |
| WO | 05/072751 A1 | 8/2005 |
| WO | 05/115245 A1 | 12/2005 |
| WO | 06/121969 A1 | 11/2006 |
| WO | 07/021964 A2 | 2/2007 |
| WO | 07/115259 A2 | 10/2007 |
| WO | 08/038281 A2 | 4/2008 |
| WO | 08/115536 A2 | 9/2008 |
| WO | 09/029958 A1 | 3/2009 |

OTHER PUBLICATIONS

Henry, et al., "Topical Anesthesia of the Bladder," Abstracts, A61.
Tyagi, et al., "Local Drug Delivery to Bladder Using Technology Innovations," Urological Clinics of North America, vol. 33 (2006), pp. 519-530, Elsevier Inc.
Fraser, et al., "The Future of Bladder Contro—Intravesical Drug Delivery, a Pinch of Pepper, and Gene Therapy," Reviews in Urology, vol. 4, No. 1 (2002).
Santus, et al, "Osmotic drug delivery: a review of the patent literature," Journal of Controlled Release, vol. 35 (1995), pp. 1-21.
Malmstrom, Per-Uno, "Intravesical therapy of superficial bladder cancer," Critical Reviews in Oncology Hematology, vol. 47 (2003), pp. 109-126, Elsevier Science.
International Search Report and Written Opinion for PCT/US2011/046439, dated Jan. 6, 2012 (8 pages).
Supplemental European Search Report issued in EP Application No. 11815265.1, dated Nov. 21, 2017 (12 pages).

* cited by examiner

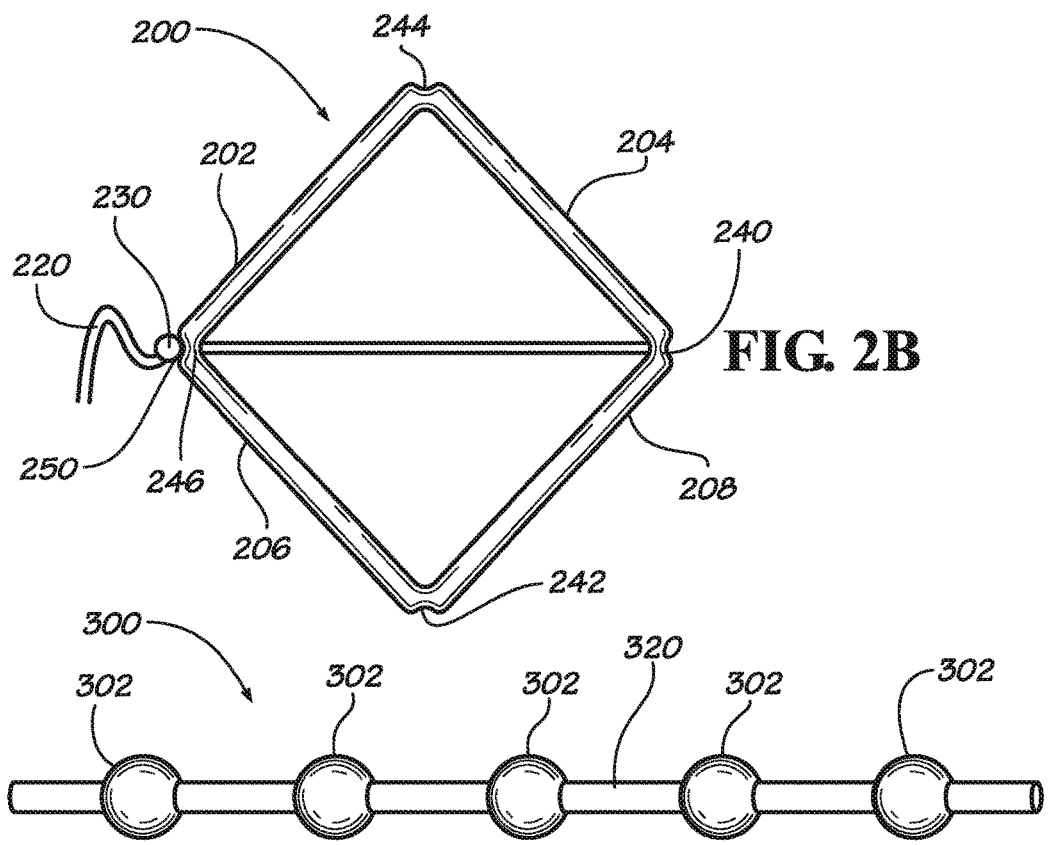
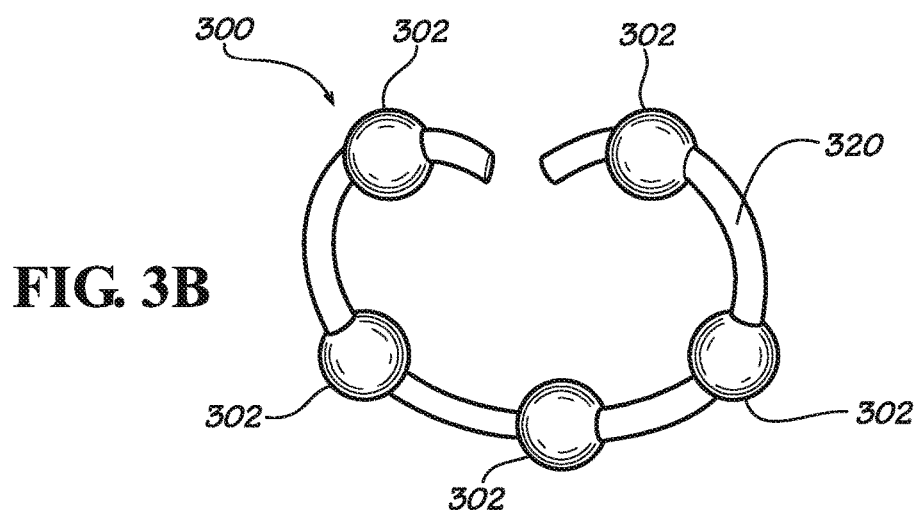

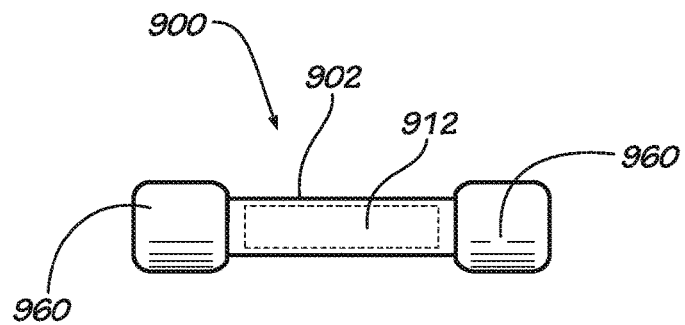
FIG. 9A
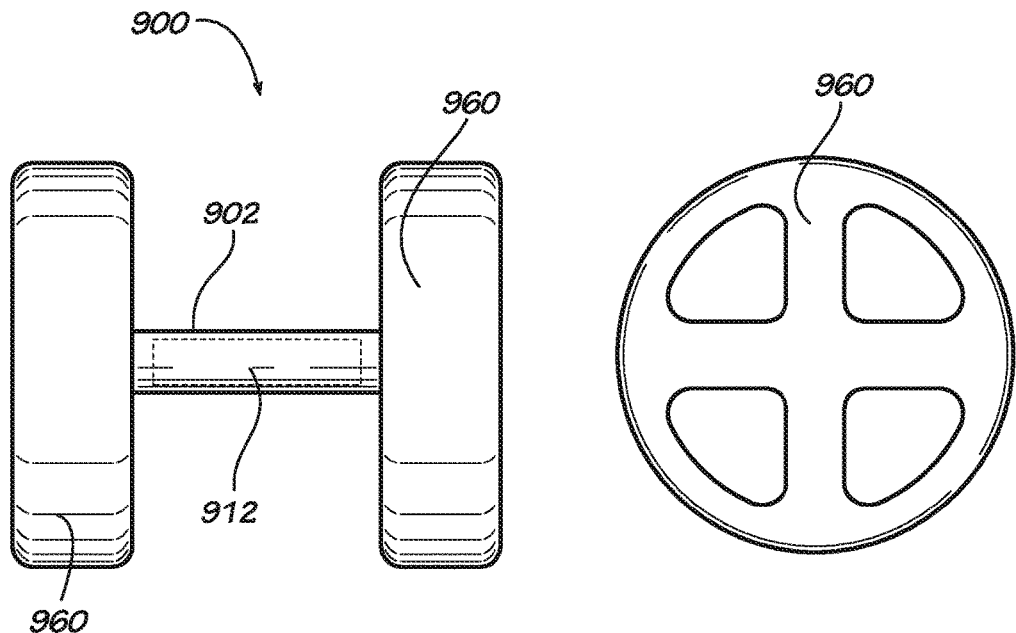
FIG. 9B   FIG. 9C

FIG. 11A
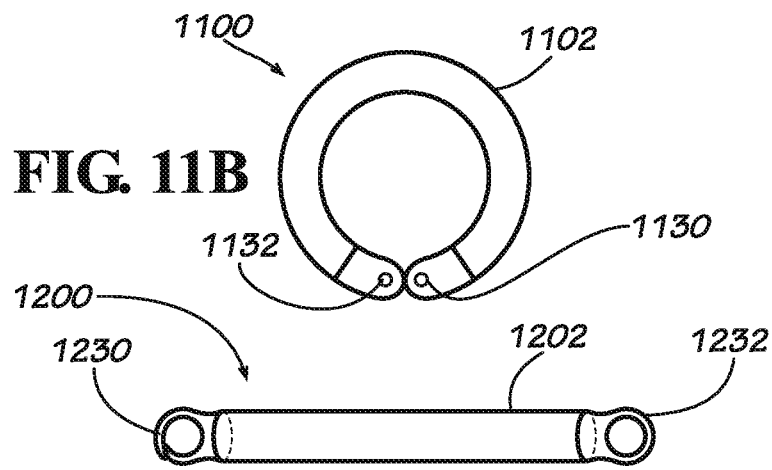
FIG. 11B
FIG. 12A
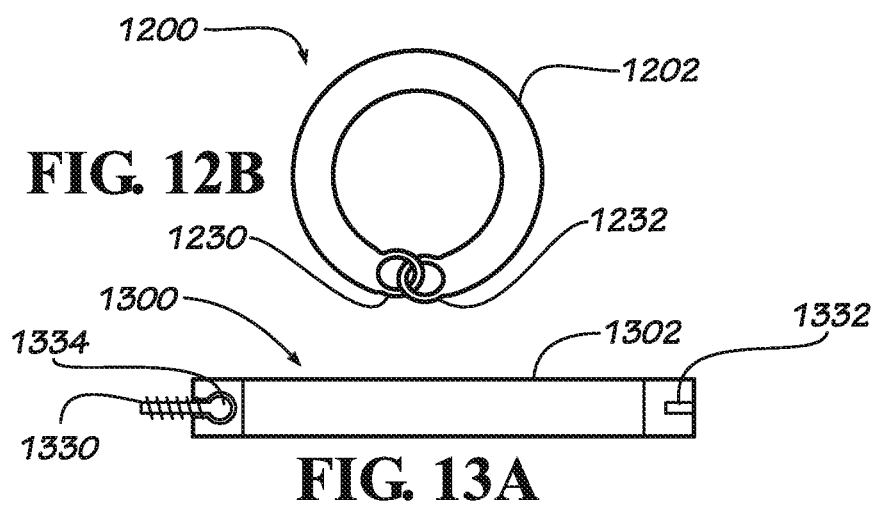
FIG. 12B
FIG. 13A
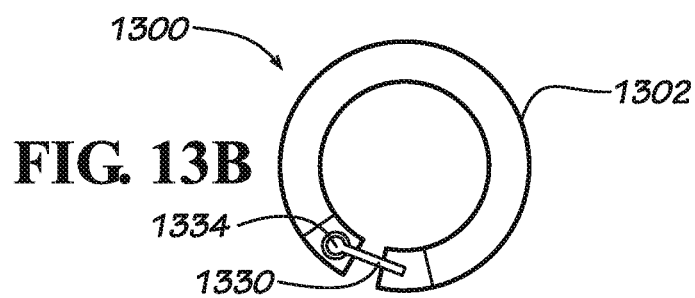
FIG. 13B

IMPLANTABLE DRUG DELIVERY DEVICES FOR GENITOURINARY SITES

CROSS-REFERENCE TO RELATED APPLICATIONS

This application is a continuation of U.S. application Ser. No. 13/813,745, filed Feb. 1, 2013, which is the U.S. national stage application of International Application No. PCT/US2011/046439, filed Aug. 3, 2011, which claims priority to U.S. Provisional Application No. 61/370,902, filed Aug. 5, 2010, which are incorporated by reference herein.

BACKGROUND

The present disclosure generally relates to implantable medical devices, and more particularly relates to implantable devices for controlled drug delivery to the bladder and other genitourinary sites.

Systems for delivering drug locally to the bladder are known. For example, instillation permits delivering a solution of drug locally to the bladder, but drawbacks are present, such as the inability to achieve continuous drug delivery over an extended period. Continuous drug delivery can be achieved from implantable devices, but many implantable devices are not suited for the bladder. For example, some implantable devices are excreted from the bladder under the forces of urination, frustrating drug delivery. Also, many implantable devices cannot fit through the urethra, preventing minimally invasive deployment through this natural pathway. Other devices may fit through the urethra in an unfilled state but must be loaded with the drug after implantation. Furthermore, many known implantable devices cannot achieve sustained and controlled delivery of a therapeutically effective amount of drug over an extended period. For example, some known devices that are small enough to be deployed through the urethra are too small to hold a sufficiently large drug payload.

A need therefore exists for implantable devices that can be deployed through a natural orifice and/or lumen of the body into a body cavity, such as through the urethra into the bladder, and can be retained in the body under expected conditions, such as within the bladder during urination. Preferably the devices provide controlled release of one or more drugs for an extended period following implantation.

BRIEF SUMMARY

Implantable drug delivery devices are provided that have a deployment shape to facilitate implantation in the body and a retention shape or retention feature to facilitate retention in the body. The device may have one or more elongated drug reservoirs containing a drug, and the drug reservoir may be formed from a deformable material. In one embodiment, a first filament is attached to the first end of the drug reservoir and second filament is attached to the second end of the drug reservoir, wherein a fastener is positioned about the first and second filaments to permit shortening and prevent lengthening of the filaments with reference to the ends of the drug reservoir, as a means for transforming the device from the implantation shape to the retention shape. This and other disclosed embodiments provided a device deployable through a natural orifice and/or lumen of the body into a body cavity, such as through the urethra into the bladder, and that can be retained in the body under expected conditions, such as within the bladder during urination, during a period of controlled release of one or more drugs.

BRIEF DESCRIPTION OF THE DRAWINGS

FIGS. 1A and 1B illustrate an embodiment of an implantable drug delivery device, wherein FIG. 1A illustrates the device in a deployment shape and FIG. 1B illustrates the device in a retention shape.

FIGS. 2A and 2B illustrate another embodiment of an implantable drug delivery device, wherein FIG. 2A illustrates the device in a deployment shape and FIG. 2B illustrates the device in a retention shape.

FIGS. 3A and 3B illustrate another embodiment of an implantable drug delivery device, wherein FIG. 3A illustrates the device in a deployment shape and FIG. 3B illustrates the device in a retention shape.

FIGS. 4A and 4B illustrate another embodiment of an implantable drug delivery device, wherein FIG. 4A illustrates the device in a deployment shape and FIG. 4B illustrates the device in a retention shape.

FIGS. 5A, 5B, and 5C illustrate another embodiment of an implantable drug delivery device, wherein FIG. 5A illustrates the device in a deployment shape, FIG. 5B illustrates the device in a retention shape, and FIG. 5C illustrates the device in an excretion shape.

FIGS. 6A and 6B illustrate another embodiment of an implantable drug delivery device, wherein FIG. 6A illustrates the device in a deployment shape and FIG. 6B illustrates the device in a retention shape.

FIGS. 7A and 7B illustrate another embodiment of an implantable drug delivery device, wherein FIG. 7A illustrates the device in a deployment shape and FIG. 7B illustrates the device in a retention shape.

FIGS. 8A and 8B illustrate another embodiment of an implantable drug delivery device, wherein FIG. 8A illustrates the device in a deployment shape and FIG. 8B illustrates the device in a retention shape.

FIGS. 9A, 9B, and 9C illustrate another embodiment of an implantable drug delivery device, wherein FIG. 9A is a cross-sectional view of the device in a deployment shape, FIG. 9B is a cross-sectional view of the device in an implanted shape, and FIG. 9C is a side view of the device in the implanted shape.

FIGS. 10A and 10B illustrate another embodiment of an implantable drug delivery device, wherein FIG. 10A illustrates the device in a deployment shape and FIG. 10B illustrates the device in a retention shape.

FIGS. 11A and 11B illustrate another embodiment of an implantable drug delivery device, wherein FIG. 11A illustrates the device in a deployment shape and FIG. 11B illustrates the device in a retention shape.

FIGS. 12A and 12B illustrate another embodiment of an implantable drug delivery device, wherein FIG. 12A illustrates the device in a deployment shape and FIG. 12B illustrates the device in a retention shape.

FIGS. 13A and 13B illustrate another embodiment of an implantable drug delivery device, wherein FIG. 13A illustrates the device in a deployment shape and FIG. 13B illustrates the device in an implanted shape.

FIGS. 14A and 14B illustrate another embodiment of an implantable drug delivery device, wherein FIG. 14A illustrates the device unanchored to the bladder wall and FIG. 14B illustrates the device anchored to a portion of the bladder wall.

FIGS. 15A and 15B illustrate another embodiment of an implantable drug delivery device, wherein FIG. 15A illustrates the device unanchored to the bladder wall and FIG. 15B illustrates the device anchored to a portion of the bladder wall.

FIGS. 16A and 16B illustrate another embodiment of an implantable drug delivery device, wherein FIG. 16A illustrates a plan view of the device and FIG. 16B illustrates a cross-sectional view of the device.

DETAILED DESCRIPTION

Figure 1A:
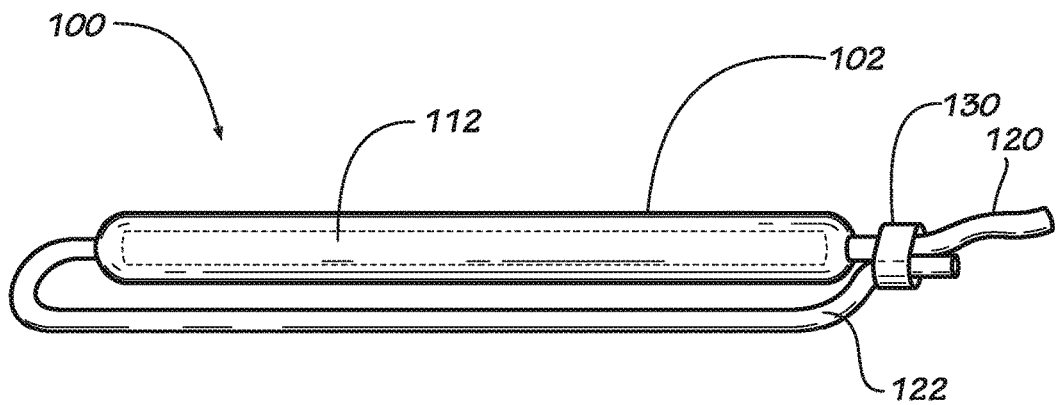

Described herein are implantable devices that can be deployed through a natural orifice or lumen of the body into a body cavity and can be retained in the body cavity once implanted. In particular embodiments, the devices can deliver drug locally to the implantation site or regionally once implanted. For the purposes of the present disclosure, the term "implantation site" generally refers to a site within the body of a human patient or other animal. The implantation site can be any genitourinary site, such as the bladder, urethra, ureters, kidneys, prostate, seminal vesicles, ejaculatory duct, vas deferens, vagina, uterus, fallopian tubes, ovaries or any other location within a urological or reproductive system of the body, among other locations. In particular embodiments, the implantation site is the bladder.

Devices for the bladder can be deployed through the urethra into the bladder in a minimally invasive deployment procedure. For example, the devices may be deployed through a deployment instrument, such as a catheter or cystoscope, that extends through the urethra to the bladder. Once implanted, the devices overcome the forces of urination to remain in the bladder, permitting drug delivery. Sustained and continuous delivery of an effective quantity of drug over an extended period may be enabled. The devices build upon those described in the following U.S. patent applications, which are incorporated by reference herein: U.S. application Ser. No. 11/463,956, filed Aug. 11, 2006; U.S. application Ser. No. 12/333,182, filed Dec. 11, 2008; U.S. application Ser. No. 12/538,580, filed Aug. 10, 2009; U.S. application Ser. No. 12/825,215, filed Jun. 28, 2010; U.S. application Ser. No. 12/825,238, filed Jun. 28, 2010; and U.S. Provisional Application No. 61/241,277, filed Sep. 10, 2009.

Embodiments of devices disclosed herein generally have at least one drug component. The drug component may include a drug and a drug reservoir. The drug may be in solid, semi-solid, or liquid form, and the drug reservoir may be a tube or other hollow structure that houses the drug. The drug reservoir may at least partially shield the drug from direct exposure to the implantation environment and may at least partially control release of the drug into the implantation environment.

The drug component also may be a solid drug form designed for extended release in response to direct exposure to the implantation environment. That is, the drug may be in a solid form that can be operably associated with a retention structure to provide controlled release of the therapeutic or prophylactic agent, without having a separate housing structure. For example, a therapeutic agent may be combined with (e.g., dispersed within) a matrix material in solid form and/or may have a controlled release coating thereon. The drug may be in the form of, for instance, a solid bead or disk that can be affixed to a retention structure.

The devices generally have a deployment shape suited for deployment through a deployment instrument placed in the urethra or another natural lumen of the body. The deployment shape may be relatively elongated or linear. For example, the device may have a reduced width with reference to its length when in the deployment shape. Although the deployment shape facilitates deployment into the body, the deployment shape may increase the likelihood of excretion of the device from the body once implanted, such as during urination. Therefore, the devices are further configured for retention in the body.

Some device embodiments are retained in the body by assuming a retention shape. The device in the retention shape occupies a larger area or volume than the device in the deployment shape, reducing the likelihood of excretion while permitting the device to free-float in the bladder. Other device embodiments are retained in the body by anchoring to a portion of the body, such as to the bladder wall. Anchoring prevents the device from free floating in the bladder, retaining the device in the bladder with reduced likelihood of excretion.

In certain embodiments, the device is associated with at least one retention structure. The retention structure may retain the device in the retention shape, or the retention structure may anchor the device to the body. Combinations of both retention modes are possible. Example retention structures include a string, wire, thread, cord, or other filament; a web, film, sheet, or other membrane; a balloon, basket, sponge, or other projection; two magnets, a hook and eye, a screw and threaded opening, or other fastener or lock; or a tether, screw, or other anchor, among others or combinations thereof.

In those embodiments in which the device achieves a retention shape, the retention structure may cause the drug component to achieve the retention shape or the retention structure itself may achieve the retention shape, either with or without changing the shape of the drug component. The retention structure may cause the device to automatically assume the retention shape once implanted, or the retention structure may be manipulated or manually adjusted after implantation to cause the device to assume the retention shape, such as with a medical instrument. The shape of the retention structure, the position of the retention structure with reference to the drug component, or both, may be altered to cause the device to assume the retention shape, and the retention structure may remain in the altered shape or position either naturally or under the influence of a fastener or lock.

For example, the retention structure may have a memorized shape that is spontaneously assumed upon implantation, such as in response to the temperature within or upon contact with urine in the bladder or in response to the removal of the confining force of the deployment instrument from the device upon escaping from the deployment instrument. Examples include a filament that can be deformed into an elongated shape for deployment and returns to a curved or coiled shape upon implantation, a membrane that can be rolled or folded into an elongated shape for deployment and returns to an expanded shape upon implantation, or a sponge that can be compressed into reduced space for deployment and expands upon exiting the deployment instrument into the bladder or upon contacting fluid therein.

The retention structure also may be manipulated or manually adjusted once the device is implanted to cause the device to assume the retention shape. Examples include a cord associated with the drug component that can be pulled to cause the drug component to change shape, a cord associated with multiple drug components that can be pulled to alter the position of the drug components with reference to each other, a filament or other structure that can be deformed into an expanded shape and maintains the shape once imparted, a balloon that can be filled, or a braided sleeve that can be expanded.

Some device embodiments are associated with an anchor structure that can anchor the device in the body, such as a movable tab, a threaded fastener, or a tether, among others. In embodiments in which the device is implanted in the bladder, the anchor structure may attach the device to the bladder wall so that the device is retained therein.

Specific embodiments will now be described by way of example. It should be understood that aspects of one of these embodiments can be combined with aspects of another of these embodiments to produce yet a further embodiment that is included within the scope of the present disclosure.

Figure 1B:
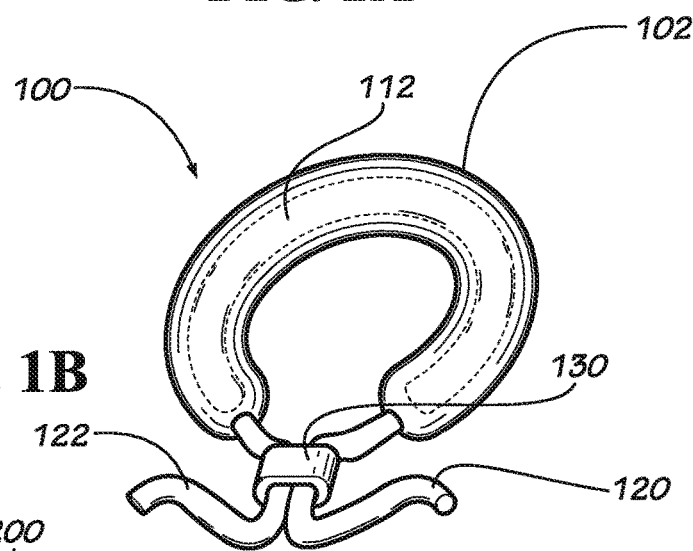

FIGS. 1A and 1B illustrate an implantable drug delivery device 100, wherein the drug component includes a drug reservoir 102 loaded with drug 112 and the retention structure includes two filaments 120, 122 associated with a fastener 130. As shown, the drug reservoir 102 is an elongated tube that can be deformed between a relatively linear deployment shape, such as the shape shown in FIG. 1A, and a relatively circular retention shape, such as the shape shown in FIG. 1B. The drug 112 may be loaded in the tube in a flexible form, so that the drug reservoir 102 can be moved between the two shapes. For example, the drug 112 may be a number of solid drug tablets, a liquid, or a gel. The filaments 120, 122 may be attached to opposite ends of the drug reservoir 102 and joined by the fastener 130. The fastener 130 can be adjusted to adjust the position of one filament 120 with reference to the other 122, thereby adjusting the position of one end of the drug reservoir 102 with reference to the other end. The device 100 can assume the retention shape by adjusting the filaments 120, 122 to draw the ends of the drug reservoir 102 closer together, and thereafter the device 100 can be retained in the retention shape by preventing adjustment of the filaments 120, 122 with the fastener 130. In such an embodiment, the device 100 is manually adjusted into the retention shape by manually adjusting the filaments 120, 122 after the device 100 is implanted.

In the illustrated embodiment, the fastener 130 is a cinch nut that permits shortening the portion of the filaments 120, 122 between the drug reservoir ends and the cinch nut, but prevents lengthening of these portions of the filaments 120, 122. Thus, the ends of the drug reservoir 102 can be drawn closer together by pulling one or both of the filaments 120, 122 through the cinch nut, causing the device 100 to assume the retention shape. Once the filaments 120, 122 have been so adjusted, the cinch nut prevents lengthening of the filaments 120, 122, retaining the device in the retention shape. Thus, manually adjusting the device 100 into the retention shape once implanted merely requires pulling one or both of the filaments 120, 122, although other fasteners 130 that require separate manipulation can be employed. Other fasteners may also be used. Examples are shown below in FIGS. 11A, 11B, 12A, 12B, 13A, and 13B.

To remove the device 100, one or both of the filaments 120, 122 may be snipped, causing the drug reservoir 102 to return to the deployment shape. Thereafter, the device 100 may be pulled through the urethra. Alternatively, all or a portion of the device 100 can be formed of a bioresorbable (e.g., biodegradable or bioerodible) material. In one case, the degradation of the device is substantial enough that it negates the need for a removal procedure, as the degradation products can be excreted. In another case, the fastener 130, filaments 120, 122, or a portion of the drug reservoir 102 is configured to degrade after a period (e.g., post drug release) to cause a break therein to release the tension holding the device 100 in the retention shape and permitting it to return to the deployment shape for retrieval through the urethra.

Figure 2A:
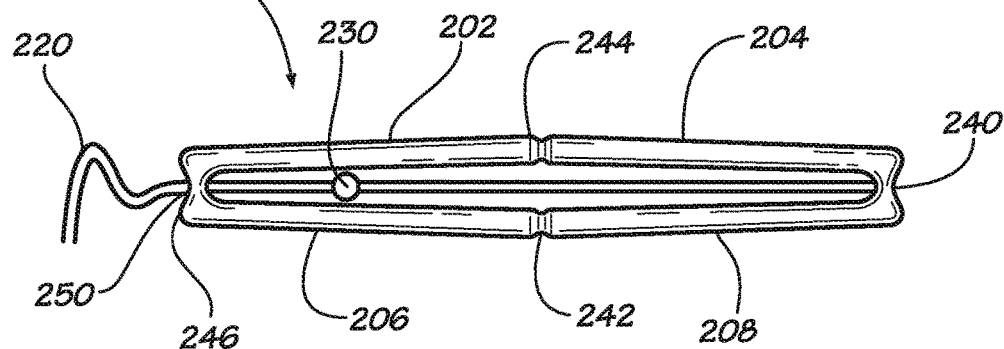

FIGS. 2A and 2B illustrate an implantable drug delivery device 200, wherein the drug component includes a number of drug reservoirs 202, 204, 206, 208 loaded with drug, and the retention structure includes a filament 220 associated with a fastener 230. As shown, the drug reservoirs 202, 204, 206, 208 are elongated tubes that are joined at their ends with joints 240, 242, 244, 246. The drug components may not be flexible, meaning one or both of the drug reservoir 202, 204, 206, 208 and the drug can be rigid. The joints 240, 242, 244, 246, however, are flexible, which permits adjusting the relative positions of the drug components with reference to each other. Thus, the device 200 can be adjusted between a relatively linear deployment shape, such as the shape shown in FIG. 2A, and a relatively expanded retention shape, such as the square shape shown in FIG. 2B.

To maintain the device 200 in the retention shape once so adjusted, the filament 230 extends from one of the joints 240 through an opening 250 in an opposite joint 246. The filament has a locking bead positioned on it, which serves as the fastener 230. The locking bead is positioned at an appropriate distance on the filament 220 such the locking bead is located within a boundary of the device 200 when the device is in the deployment shape and outside of the device boundary when the device 200 is in the retention shape. Although the locking bead is sized slightly larger than the opening 250, the structure defining the opening 250 has sufficient flexibility such that the locking bead can pass through the opening 250 when the filament 230 is forcefully pulled. Thereafter, the opening 250 returns to a position that prevents passage of the locking bead, maintaining the relative positions of the drug reservoirs 202, 204, 206, 208 to retain the device 200 in the retention shape. Thus, moving the device 200 from the deployment shape to the retention shape merely requires pulling the filament 220 until the locking bead passes through the opening 250. It should be noted that four elongated, tubular drug reservoirs 202, 204, 206, 208 are shown by way of example, although a different number or shape of drug reservoirs could be used. Further, the drug reservoirs 202, 204, 206, 208 may be locked in position using a fastener 230 other than a filament associated with a locking bead.

FIGS. 3A and 3B illustrate an implantable drug delivery device 300, wherein the drug component includes a number of drug beads 302, and the retention structure includes a filament 320. The drug beads 302 are positioned along the filament 320. The beads 302 provide controlled release of the drug in vivo. In one embodiment, the drug bead is in the form of a bioresorbable matrix material in which a drug is dispersed. In another embodiment, the bead may be a compressed drug tablet having a bioresorbable coating thereon. Five spherical drug beads 302 are shown in FIGS. 3A and 3B, although any number or shape may be used. The drug beads 302 also could be substituted with drug reservoirs housing a drug, or a combination of drug bead and drug reservoirs could be used to provide complementary drug release profiles (e.g., one or more units for immediate release with one or more units for delayed release).

The filament 320 is formed from a shape-memory material that is preprogrammed to assume a retention shape but can be deformed or adjusted into other shapes. Thus, the device 300 can be adjusted into a relatively linear deployment shape, such as the shape shown in FIG. 3A, and upon exiting the deployment instrument into the bladder, the device 300 automatically assumes the relatively expanded and curved retention shape, such as the shape shown in FIG. 3B. It should be noted that the illustrated retention shape is merely one example. In other embodiments, the filament may be preprogrammed to assume other non-linear, expanded shapes. The filament 320 also may be formed from a material that does not have shape memory but instead can maintain an imparted shape once manipulated. In such cases, the filament is manually adjusted into the retention shape once implanted in the bladder.

Figure 4A:
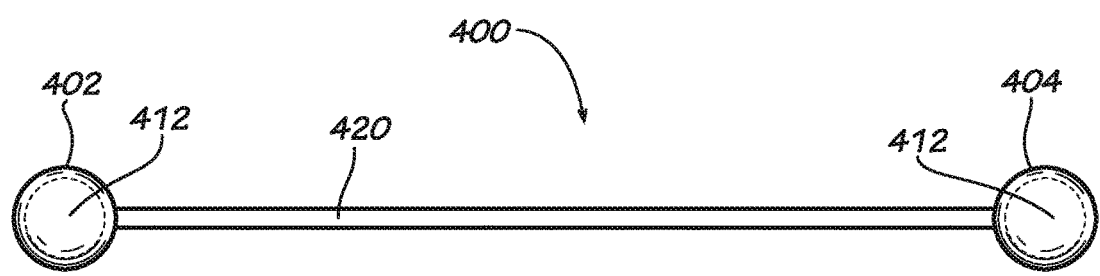
Figure 4B:
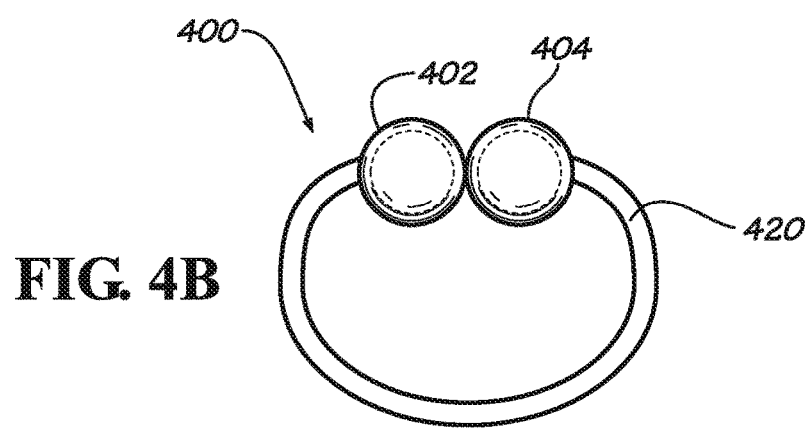

FIGS. 4A and 4B illustrate another implantable drug delivery device 400, wherein the retention structure includes a filament 420 and the drug component includes drug reservoirs 402, 404 loaded with drug 412 positioned on ends of the filament 420. Two spherical drug reservoirs 402, 404 are shown, although any number or shape may be used. The filament 420 may be formed from an elastic wire that is preprogrammed to assume a retention shape but can be deformed or adjusted into other shapes. Thus, the device 400 may be adjusted into a relatively linear deployment shape, such as the shape shown in FIG. 4A, and upon exiting the deployment instrument into the bladder, the device 400 may automatically assume the relatively expanded and curved retention shape, such as the shape shown in FIG. 4B. The illustrated retention shape is merely one example, as the filament may be preprogrammed to assume other non-linear, expanded shapes. The filament 420 also may be formed from a shape-memory material other than elastic wire, or from a material that does not have shape memory but instead can maintain an imparted shape once manipulated. In such cases, the filament may be manually adjusted into the retention shape in the bladder.

Figure 5A:
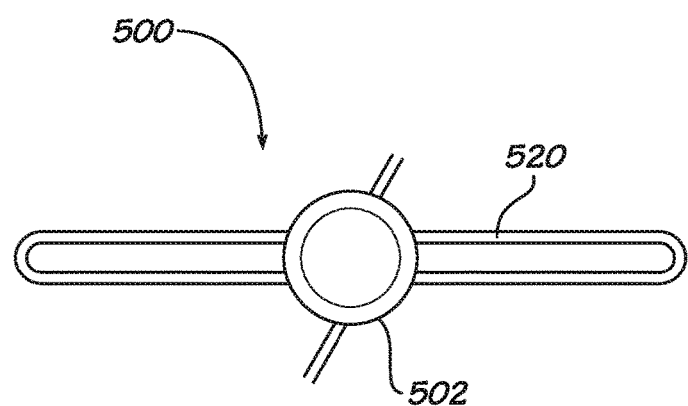
Figure 5B:
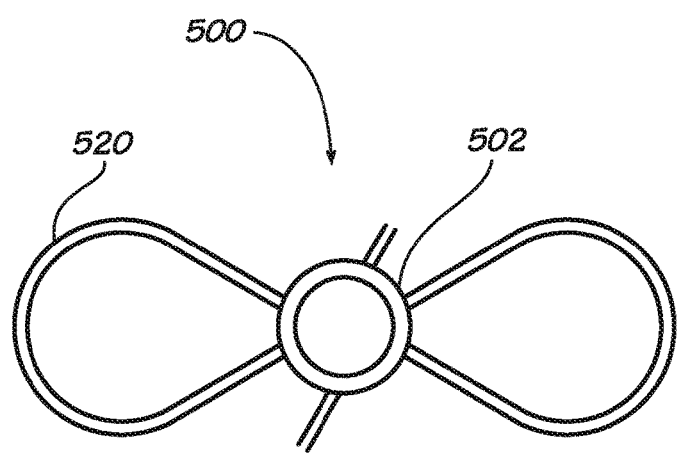
Figure 5C:

FIGS. 5A, 5B, and 5C illustrate an implantable drug delivery device 500, wherein the drug component includes a drug disk 502, and the retention structure includes a filament 520. The drug disk 502 is positioned on the filament 520 such that ends or other portions of the filament 520 are embedded in the disk 502. The drug disk 502 may be constructed with a bioresorbable matrix material and/or a coating to provide controlled release of the drug, much like the drug beads described above with reference to FIGS. 4A and 4B. The filament 520 may be formed from a shape-memory material that is preprogrammed to assume a retention shape. Thus, the filament 520 may be adjusted into a relatively linear deployment shape, such as the shape shown in FIG. 5A, and upon exiting the deployment instrument into the bladder, the filament 520 may automatically assume a relatively expanded retention shape, such as the "figure eight" shape shown in FIG. 5B. Upon absorption of the drug disk 502, the ends or other embedded portions of the filament 520 are released, causing the filament 520 to return to an elongated configuration, shown in FIG. 5C, for excretion from the bladder. Thus, the device 500 may not require a medical procedure to be removed. It should be noted that, in other embodiments, the drug disk can have other shapes and the retention shape may be other than a figure eight.

Figure 6A:
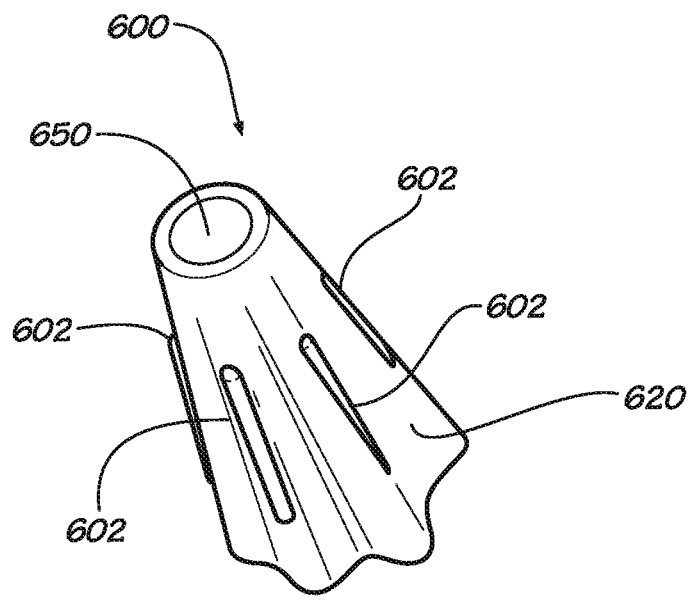
Figure 6B:
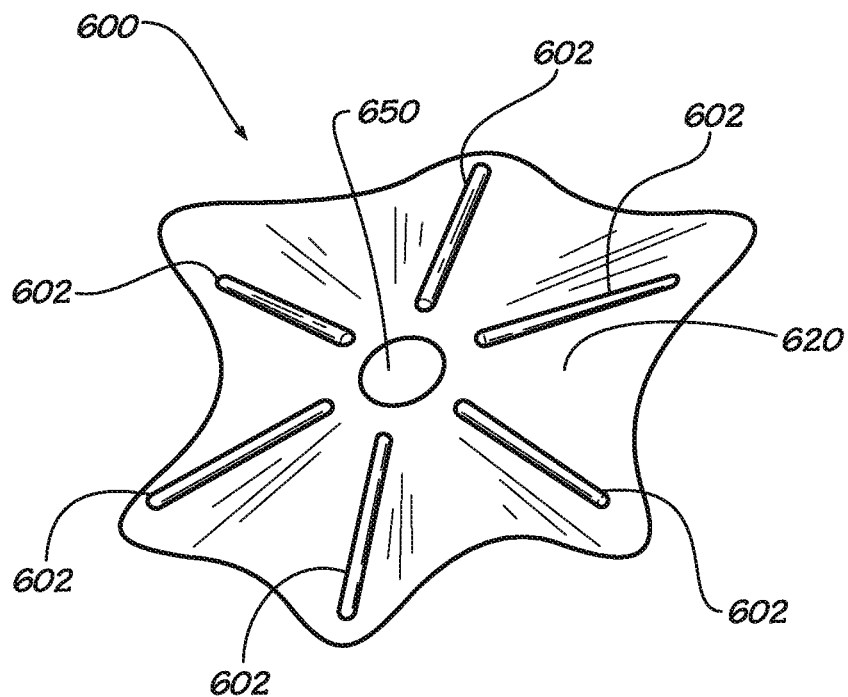

FIGS. 6A and 6B illustrate an implantable drug delivery device 600, wherein the retention structure is a flexible web 620 and the drug components are embedded in the web. The web 620 may be deformed into a folded deployment shape, shown in FIG. 6A, and upon exiting the deployment instrument into the bladder, the web may automatically assume the relatively, flat expanded shape shown in FIG. 6B. For example, the flexible web 620 may be elastic and may naturally have a substantially flat shape (in the absence of compressive forces). A relief opening 650 may or may not be provided in a central portion of the web 620 to facilitate folding and reduce bunching of the web 620 when in the deployment shape. The relief opening 650 also may permit urine to flow through the web 620 once implanted in the bladder. In certain embodiments, additional relief openings are provided through other portions of the web so that greater fluid flow is permitted. As shown, the web 620 may be somewhat star-shaped and the drug components may be elongated drug reservoirs 602 that extend radially outward about the web 620. However, other web shapes and other drug reservoir numbers, shapes and positions can be used.

Figure 7A:
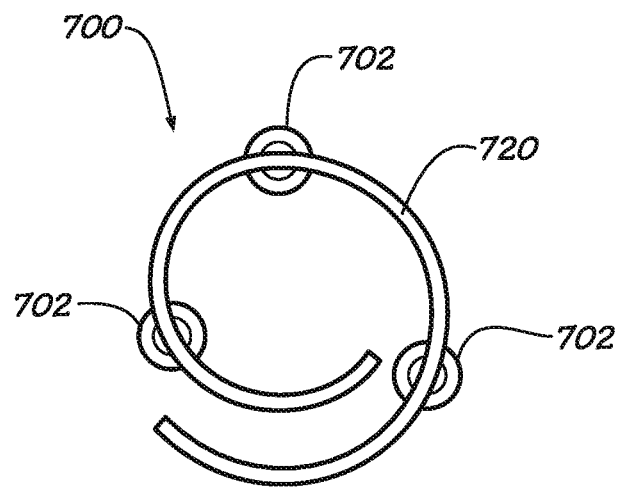
Figure 7B:
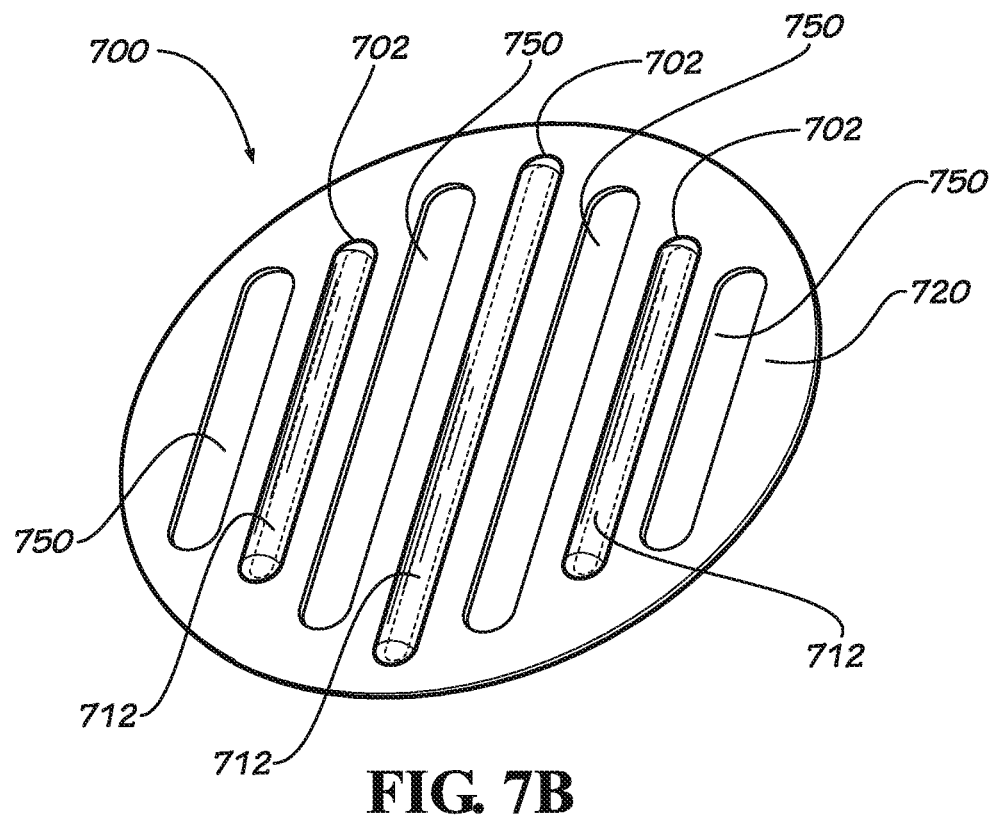

For example, FIGS. 7A and 7B illustrate another implantable drug delivery device 700, wherein the retention structure is a web 720 that is relatively circular in shape. The web 720 has elongated relief openings 750 formed through its surface, aligned with each other. The relief openings 750 are interspaced with drug reservoirs 702 loaded with drug 712 embedded in the web 720. The web 720 may be rolled into a deployment shape, shown in FIG. 7A, and upon exiting the deployment instrument into the bladder, the web 720 may automatically assume the relatively, flat expanded shape shown in FIG. 7B.

In various embodiments of the devices shown in FIGS. 6A, 6B, 7A, and 7B, the web may be formed of a biocompatible flexible polymeric sheet. The sheet may be bioresorbable. The solid drug components may be attached to the outside surface(s) of the web, or they may be integrated into a drug reservoir formed in the web. For example, the drug reservoir may be in the form of a space formed entirely or partially by the web. In one case, the drug component is sandwiched between two thin sheets that are stacked and adhered together about a periphery of each drug component. In another case, the drug components are secured in grooves or within elongated apertures in the web. The drug components may be in the form of solid drug rods, which may be constructed of a bioresorbable matrix material (mixed with a drug) and/or a coating to provide controlled release of the drug. Such drug rods may be formed by casting or compression molding, for example, of drug alone or in combination with one or more binders or other excipients.

Figure 8A:
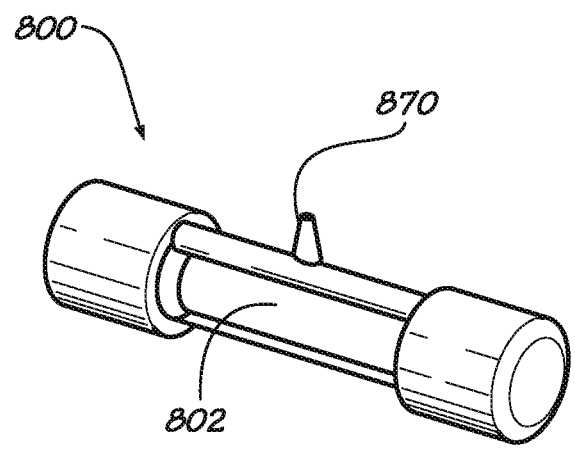
Figure 8B:
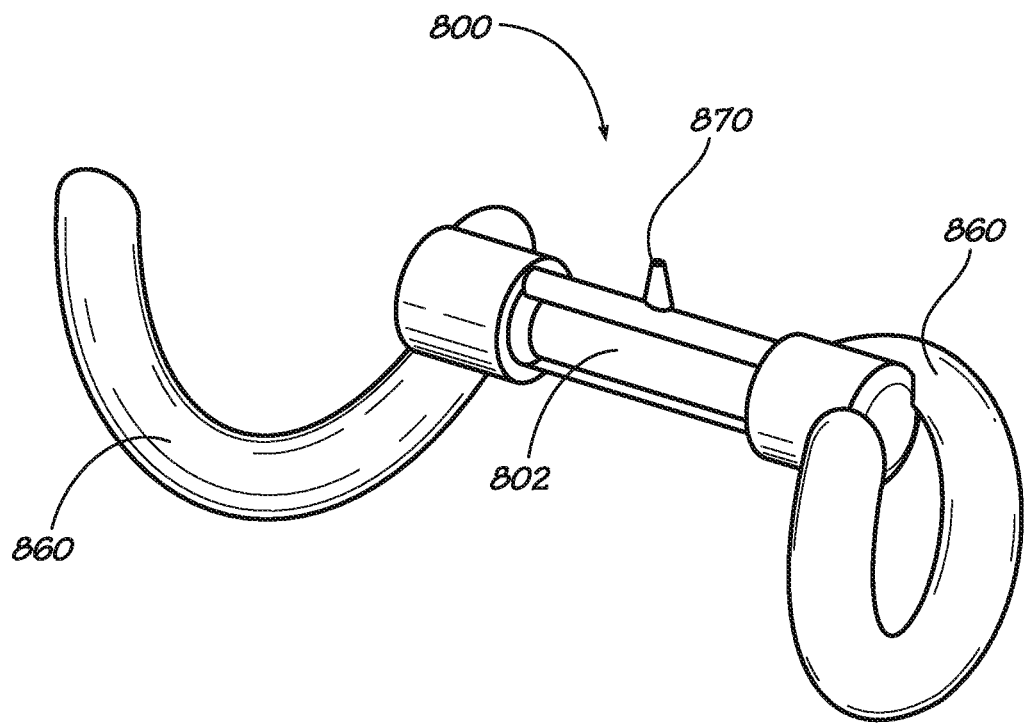

FIGS. 8A and 8B illustrate another implantable drug delivery device 800, wherein the drug component is a drug reservoir 802 loaded with drug, and the retention structure includes a number of inflatable balloons 860 in communication with an inflation port 870. The drug component may be elongated and may or may not be deformable, either due to the rigidity of the drug reservoir 802 or the drug. When the balloons 860 are not inflated, the device 800 takes on a relatively linear deployment shape, such as the shape shown in FIG. 8A, and when the balloons 860 are inflated, the device 800 assumes a retention shape, such as the shape shown in FIG. 8B. The balloons may be inflated by directing a fluid (e.g., air, saline) through the inflation port 870 after the device 800 is implanted. In the illustrated embodiment, two balloons 860 are positioned on opposite ends of the drug reservoir 802, and the balloons 860 assume arched or hooked shapes upon inflation, although other numbers, positions, and inflated shapes can be used. The inflated balloons 860 may advantageously enhance the buoyancy of the device 800 within the bladder.

FIGS. 9A, 9B, and 9C illustrate another implantable drug delivery device 900, wherein the drug component is a drug reservoir 902 loaded with drug 912, and the retention structure includes a number of sponges 960. The drug component may be elongated and may or may not be deformable, either due to the rigidity of the drug reservoir 902 or the drug 912. The sponges 960 may be capable of assuming a reduced volume, either when compressed or in a dehydrated state. When the sponges 960 are compressed, or are in a dehydrated state, the device 900 takes on a relatively linear deployment shape, such as the shape shown in FIG. 9A, and when the sponges 960 are expanded, or hydrated, the device 900 assumes a retention shape, such as the shape shown in FIG. 9B. The sponges 960 may automatically expand upon exiting the deployment instrument or in response to contacting and absorbing fluid in the bladder. In the illustrated embodiment, two sponges 960 are positioned on opposite ends of the drug reservoir 902, and the sponges 960 assume wheel shapes upon expansion, although other numbers, positions, and expanded shapes can be used. In some embodiments, the sponges may be formed of a bioresorbable material that after swelling will degrade over time.

Figure 10A:
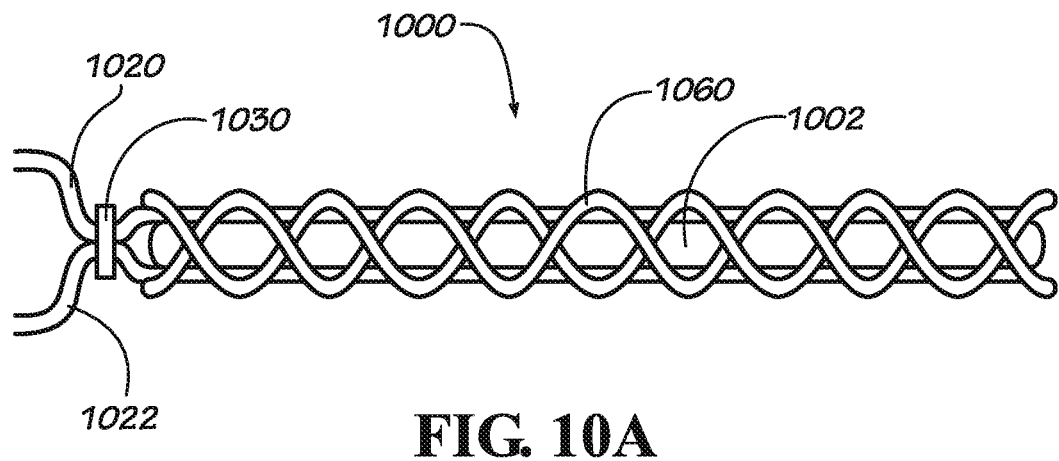
Figure 10B:
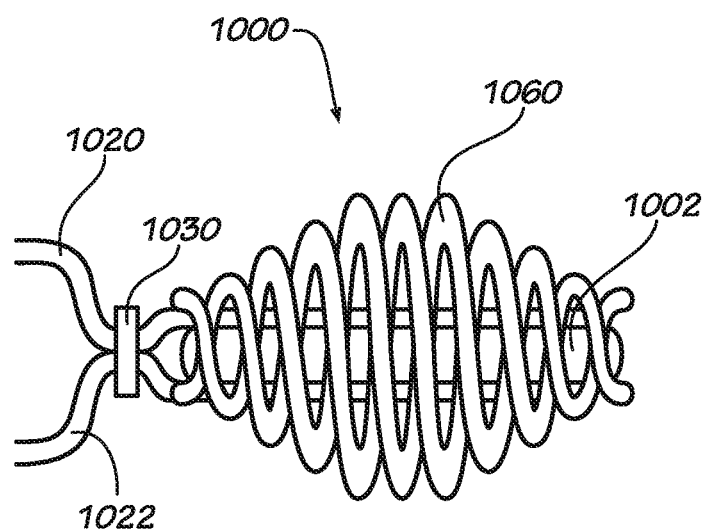

FIGS. 10A and 10B illustrate an implantable drug delivery device 1000, wherein the drug component includes a drug reservoir 1002 loaded with drug and the retention structure includes a braided basket 1060 associated with two filaments 1020, 1022 and a fastener 1030. The drug reservoir 1002 is an elongated tube that can be compressed along its length, much like a bellows. The drug may be loaded in the drug reservoir 1002 in a flexible form, so that the drug reservoir 1002 can be compressed along its length. For example, the drug may be a number of solid drug tablets, a liquid, or a gel. The braided basket 1060 may be positioned about the exterior of the drug reservoir 1002, attached to the drug reservoir 1002 via the filaments 1020, 1022, which extend along opposite sides of the drug reservoir 1002 between the drug reservoir 1002 and the braided basket 1060. The filaments 1020, 1022 are joined together at one end of the device 1000 with the fastener 1030.

The device 1000 generally assumes an elongated deployment shape, shown in FIG. 10A. Once implanted, the filaments 1020, 1022 can be pulled to reduce the length of the drug reservoir 1002, causing the braided basket 1060 to expand outward about its exterior, such that the device 1000 assumes the retention shape shown in FIG. 10B. Thereafter the device 1000 can be retained in the retention shape by preventing adjustment of the filaments 1020, 1022 with the fastener 1030. In such an embodiment, the device 1000 is manually adjusted into the retention shape by manually adjusting the filaments 1020, 1022 after the device 1000 is implanted.

In the illustrated embodiment, the fastener 1030 is a cinch nut that permits shortening but prevents lengthening the filaments 1020, 1022. Thus, the braided basket 1060 and drug reservoir 1002 can be drawn into a reduced length by pulling the filaments 1020, 1022 through the cinch nut, causing the device 1000 to assume the retention shape. Once the filaments 1020, 1022 have been so adjusted, the cinch nut prevents lengthening of the filaments 1020, 1022, retaining the device 1000 in the retention shape. Thus, manually adjusting the device 1000 into the retention shape once implanted merely requires pulling the filaments 1020, 1022, although other fasteners that require separate manipulation can be employed.

To remove the device 1000, the filaments 1020, 1022 may be snipped, causing the drug reservoir 1002 to return to the deployment shape. Thereafter, the device 1000 may be pulled through the urethra. Alternatively, all or a portion of the device 1000 can be formed of a bioresorbable material, such as described above with reference to FIGS. 1A and 1B, so that a retrieval procedure is unnecessary.

FIGS. 11A, 11B, 12A, 12B, 13A, and 13B illustrate implantable drug delivery devices 1100, 1200, 1300, wherein the drug component is a drug reservoir 1102, 1202, 1302 loaded with drug, and the retention structure is a two-part fastening or locking device having its two parts positioned on opposite ends of the drug reservoir. For example, the two-part fastening or locking device can be two magnets 1130, 1132 associated with opposite ends of the drug reservoir 1102, as shown in FIGS. 11A and 11B, a hook 1230 and an eye loop 1232 associated with opposite ends of the drug reservoir 1202, as shown in FIGS. 12A and 12B, or a screw 1330 and threaded opening 1332 associated with opposite ends of the drug reservoir 1302, as shown in FIGS. 13A and 13B. The drug reservoir 1102, 1202, 1302 is an elongated tube that can be deformed between a relatively linear deployment shape, shown in FIGS. 11A, 12A, and 13A, and a relatively circular retention shape shown in FIGS. 11B, 12B, and 13B. Once the device 1100, 1200, 1300 is implanted, the two parts of the two-part fastening device can be associated with each other to maintain the device 1100, 1200, 1300 in the retention shape. For example, the magnets 1130, 1132 can be joined together as shown in FIG. 11B, the hook 1230 can be attached to the eye loop 1232, as shown in FIG. 12B, and the screw 1330 can be threaded into the threaded opening 1332, as shown in FIG. 13B. In particular, the screw 1330 is engaged about a central portion and is rotated to thread the screw 1330 into the threaded opening 1332, as the head 1334 of the screw may be housed in a cavity in the drug reservoir 1302 that is sized and shaped to permit free rotation of the head 1334 with reference to the drug reservoir 1302.

Figure 14A:
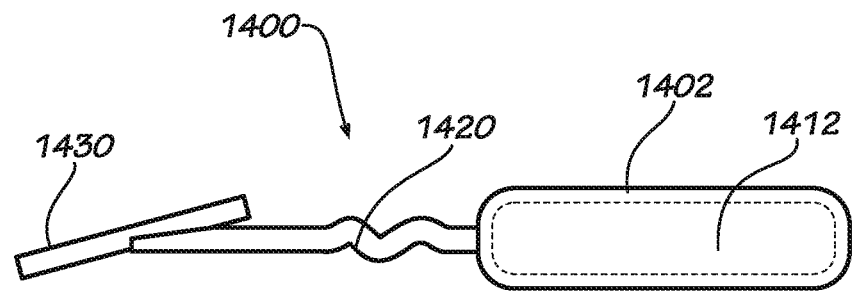
Figure 14B:
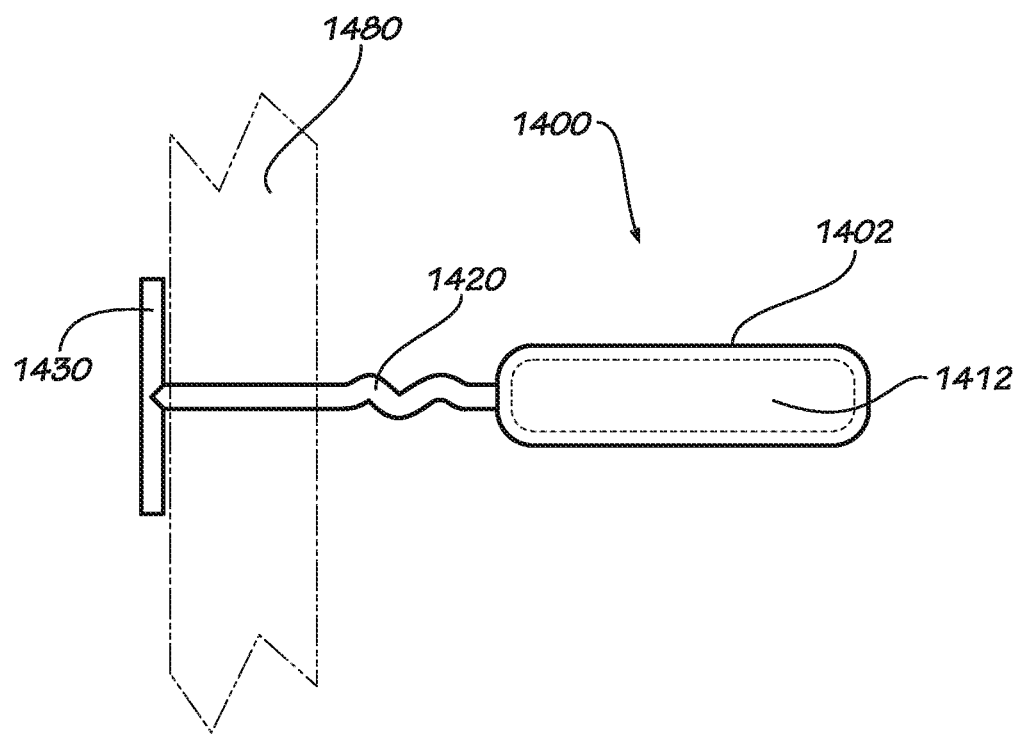

FIGS. 14A and 14B illustrate an implantable drug delivery device 1400, wherein the drug component is a drug reservoir 1402 loaded with drug 1412, and the retention structure is an anchor 1430 connected via tether 1420 to the drug reservoir 1402. The anchor 1430 may be T-shaped and may fold downward for deployment through the deployment instrument into the bladder, as shown in FIG. 14A. Once in the bladder, the anchor 1430 engages the bladder wall 1480 to anchor the device 1400 therein, as shown in FIG. 14B. Anchors with other configuration may be used, or the anchor may be omitted completely, in which case the tether may be attached to the bladder wall using a mucoadhesive material known in the art. In some embodiments, the anchor 1430 may be bioresorbable so that the anchor 1430 does not need to be removed, in which case the device 1400 can be removed by cutting the tether 1420 and extracting the drug reservoir 1402 from the bladder. Alternatively, the drug reservoir 1402 also may be bioresorbable, or the drug reservoir 1402 may be substituted with a solid drug form that is not housed in a drug reservoir. The tether 1420 may be either bioresorbable or excretable, so that the device 1400 is completely resorbable or does not otherwise require separate removal.

Figure 15A:
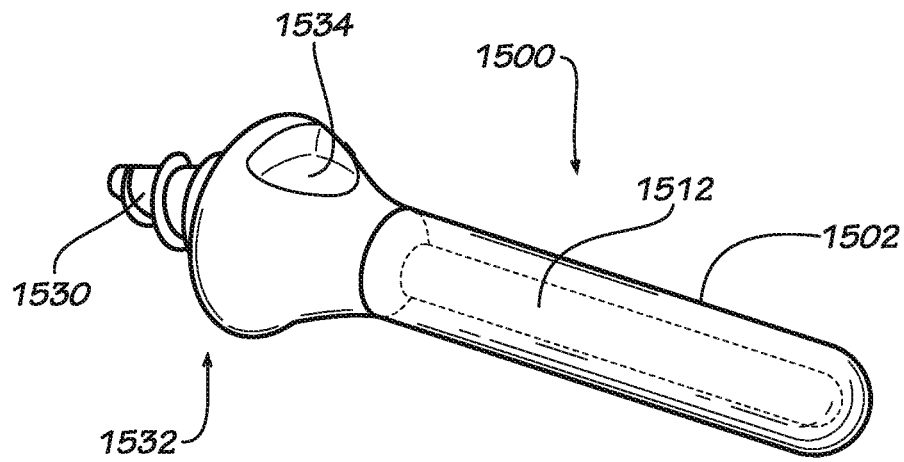
Figure 15B:
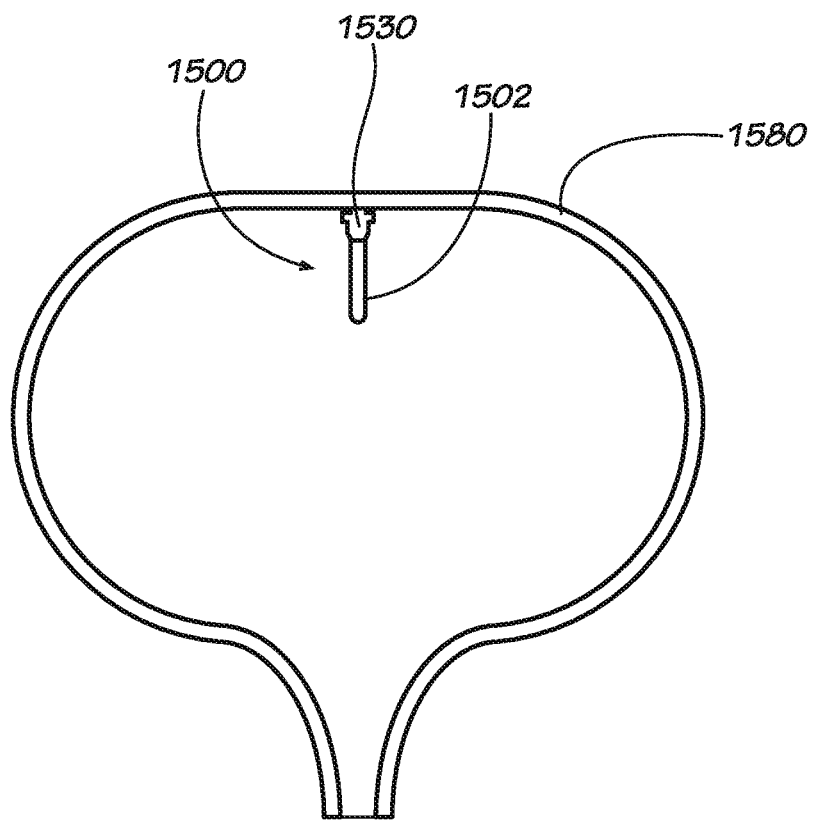

FIGS. 15A and 15B illustrate an implantable drug delivery device 1500, wherein the drug component is a drug reservoir 1502 loaded with drug 1512, and the retention structure is a threaded anchor 1530 positioned on one end of the drug reservoir 1502. The entire device 1500 may be elongated, as shown in FIG. 15A, for deployment through a deployment instrument. Once in the bladder, the anchor 1530 may threadingly engage the bladder wall 1580 to anchor the device therein, as shown in FIG. 15B. In some embodiments, the threaded anchor 1530 may be configured for easy grasping with an insertion instrument. For example, the threaded anchor 1530 may be attached to the drug reservoir 1502 at a head portion 1532, which may include detents 1534 that facilitate engaging the device 1500 with forceps or another insertion tool. The threaded anchor 1530 also may be omitted, in which case the drug reservoir 1502 may be attached to the bladder wall using a mucoadhesive material.

Figure 16A:
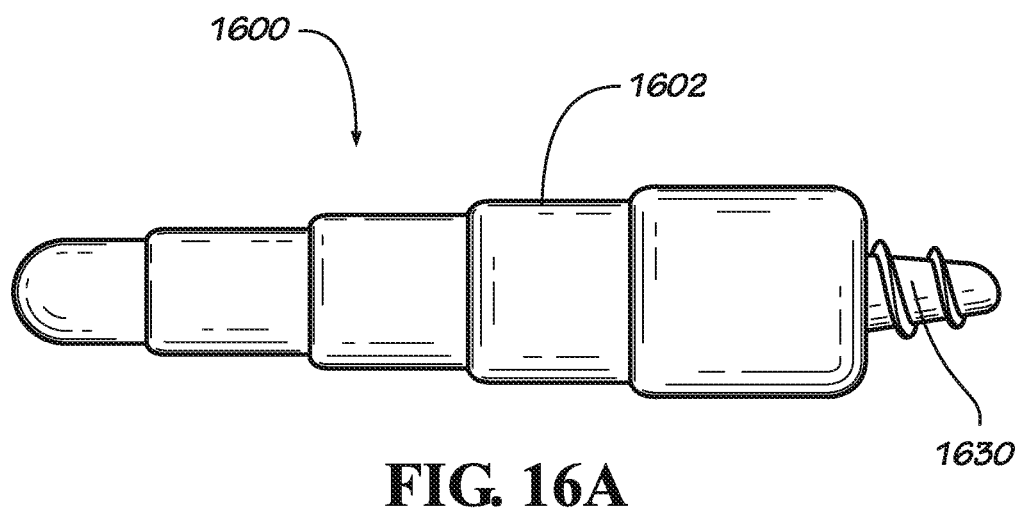
Figure 16B:
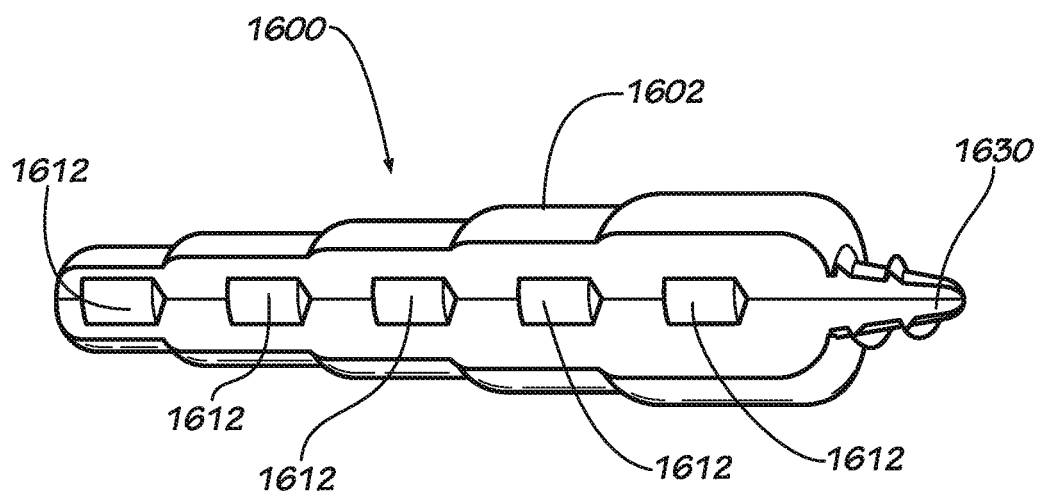

FIGS. 16A and 16B illustrate an implantable drug delivery device 1600, wherein the drug component includes a drug reservoir 1602 housing a number of drug doses 1612, and the retention structure is a threaded anchor 1630 positioned on one end of the drug reservoir 1602. The entire device 1600 may be elongated, as shown in FIG. 16A, for deployment through a deployment instrument. Once in the bladder, the threaded anchor 1630 may threadingly engage the bladder wall to anchor the device 1600 therein. The drug reservoir 1602 is formed from a bioresorbable material that can degrade in the implantation environment. The drug reservoir 1602 is shaped so that the material thickness increases along the length of the device 1600, either uniformly or in a stepped fashion as shown in FIG. 16A. A number of drug doses 1612 are housed within the material, as shown in FIG. 16B, and the drug doses 1612 are exposed as the material degrades. Because the drug reservoir 1602 degrades at a varying rate along the length of the device 1600 due to the variation in material thickness, the drug doses 1612 are released at varying rates.

Figure 17:
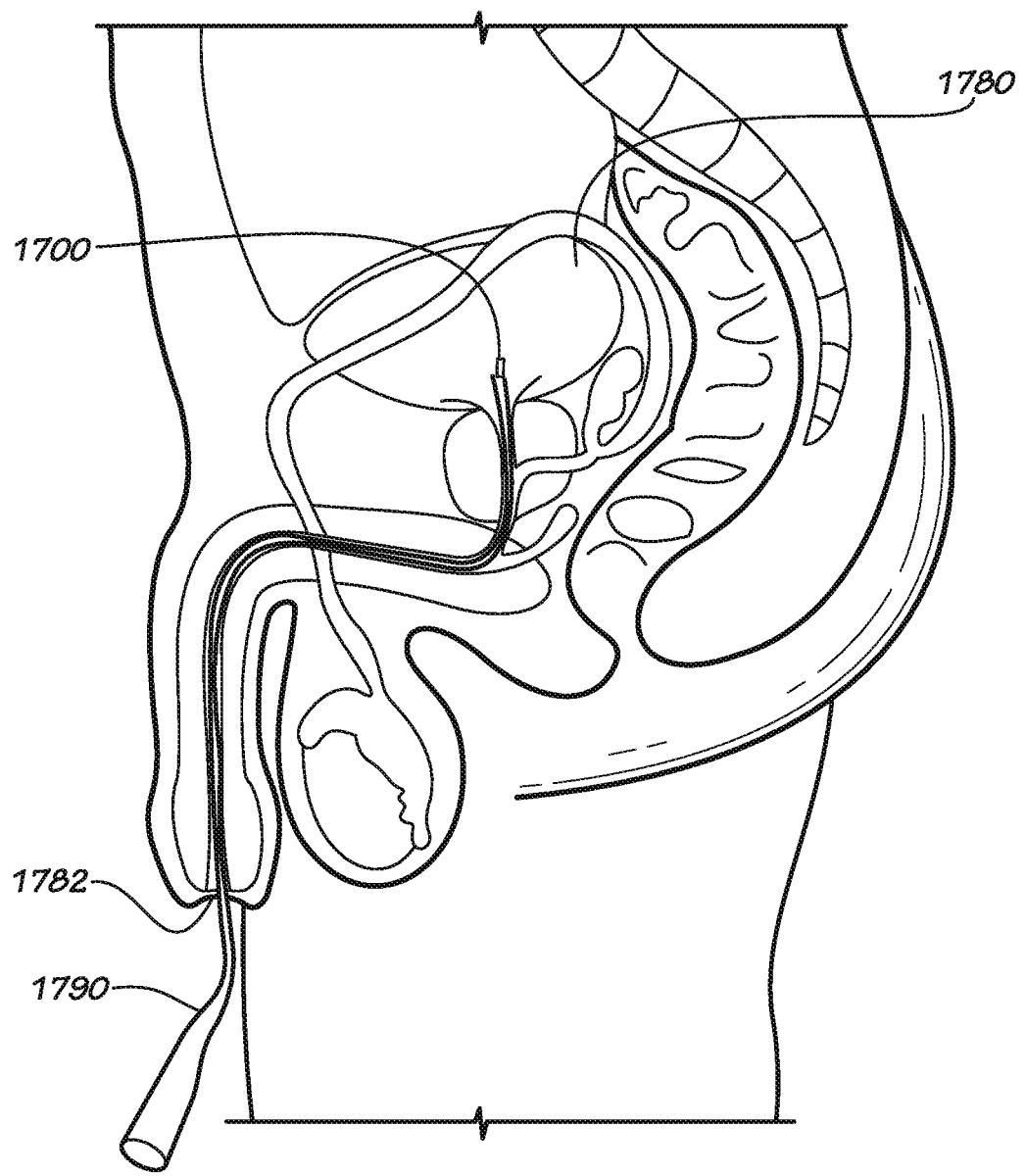
FIG. 17 is a sagittal view of a male genitourinary system, illustrating a drug delivery device being deployed into the bladder.

FIG. 17 is a sagittal view of a male genitourinary system, illustrating an implantable drug delivery device 1700 being deployed through a deployment instrument 1790 into an implantation site. By way of example, the male anatomy is shown and the implantation site is shown as the bladder 1780. The drug delivery device 1700 may be an embodiment of one of the implantable drug delivery devices described herein. The deployment instrument 1790 may be any device designed to navigate natural lumens of the body to reach the intended implantation site. For deployment in the bladder 1780, the deployment instrument 1790 is sized and shaped for passing through a urethra 1782 of a patient to a bladder 1780 as shown. The deployment instrument 1790 may be a known device, such as a catheter or cystoscope, or a specially designed device, such as an one of the deployment instruments described in U.S. Provisional Application No. 61/241,229, filed on Sep. 10, 2009, or U.S. Provisional Application No. 61/311,103, filed on Mar. 5, 2010, each of which is incorporated herein by reference. The deployment instrument 1790 is used to deploy the implantable device 1700 into the body and is subsequently removed from the body, leaving the implantable device 1700 wholly implanted in the body, either free-floating therein or anchored thereto. Once so implanted, the device 1700 may release drug into the body for an extended period. A comparable procedure can be used to deploy any of the devices described herein into other parts of the body through other natural lumens.

Figure 18:
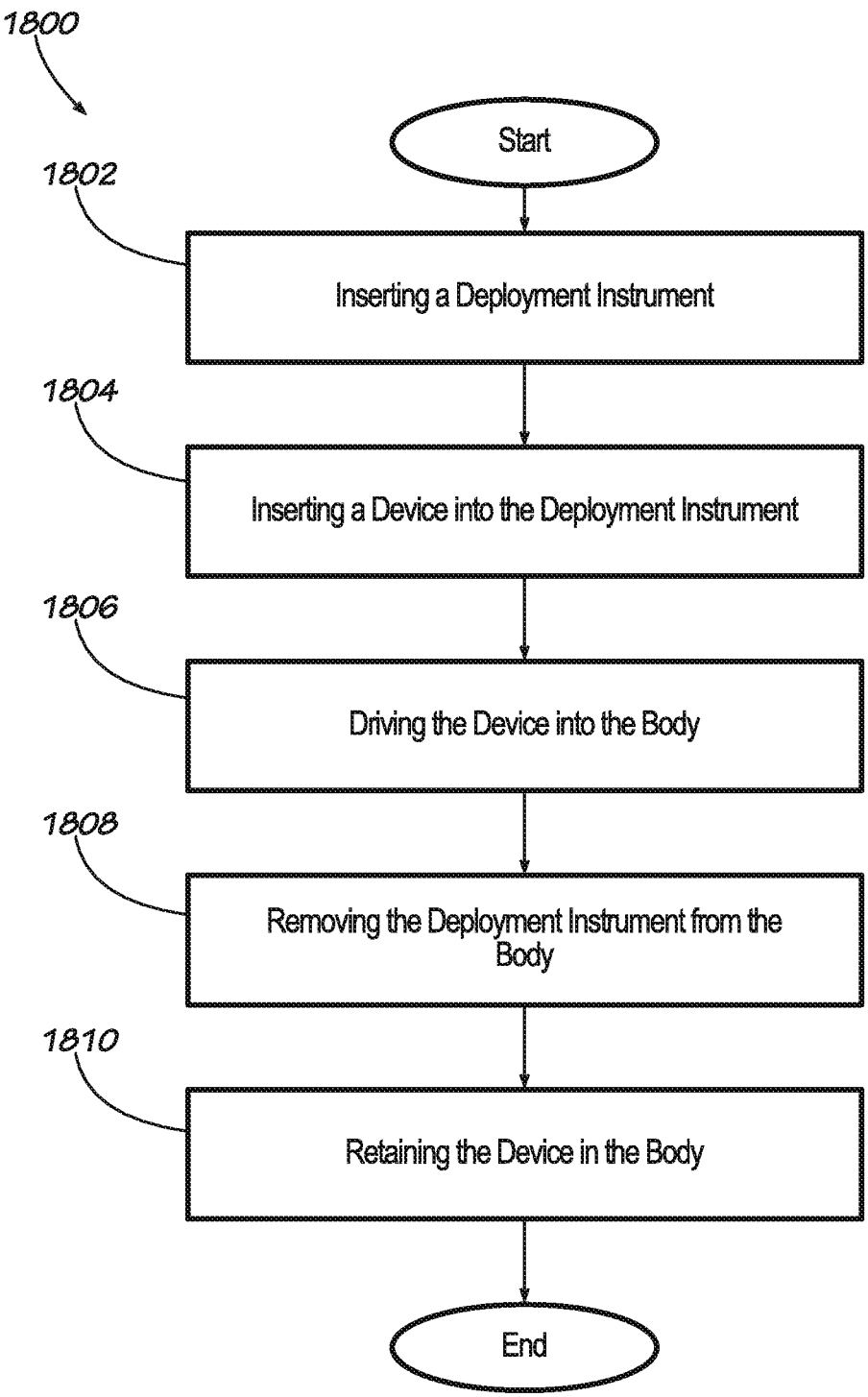
FIG. 18 is a block diagram illustrating an embodiment of a method for implanting an implantable device into the bladder.

FIG. 18 is a block diagram illustrating an embodiment of a method 1800 for implanting an implantable device into the bladder, such as an embodiment of one of the implantable drug delivery devices described herein. In block 1802, a deployment instrument is inserted into the body. The deployment instrument may be inserted into the urethra and driven forward until a distal end of the deployment instrument is positioned in the bladder while a proximal end remains outside of the body.

In block 1804, the device is inserted into the deployment instrument. In some cases, inserting the device into the deployment instrument can include deforming the device from a retention shape to a deployment shape. In some cases, the order of blocks 1802 and 1804 is reversed.

In block 1806, the device is driven into the bladder. Driving the device from the deployment instrument removes the force of the deployment instrument wall from the device, which may cause the device to naturally return to a retention shape for retention in the bladder. Alternatively, the device may be manipulated into a retention shape or the device may be anchored in the bladder.

In block 1808, the deployment instrument is removed from the body. Thereafter, in block 1810, the device is retained within the body. The device either free floats in the bladder or is anchored therein to the bladder wall. The device may be retained for an extended period, such as a period of hours, days, weeks, or months. In embodiments in which the device is an implantable drug delivery device, the device remains implanted to release drug from the device into the bladder, such as to the urothelial tissues and other local or regional tissues. Subsequently, the device may be removed or resorbed.

The devices described herein can be used to deliver essentially any drug or combination of drugs for treatment or prophylaxis of a variety of conditions and diseases. In a certain application, the devices are useful for treatment of genitourinary tissue sites. In one embodiment, the implantable drug delivery device is used to provide pain relief to the patient. In other embodiments, the drug delivery device is used to treat inflammatory conditions such as interstitial cystitis, radiation cystitis, painful bladder syndrome, prostatitis, urethritis, post-surgical pain, and kidney stones. In still other embodiments, the drug delivery device is used to treat urinary incontinence, frequency, or urgency, including urge incontinence and neurogenic incontinence, as well as trigonitis. In yet another embodiment, the drug delivery device is used to treat urinary tract cancer, such as bladder cancer and prostate cancer. In still another embodiment, the drug delivery device is used to treat infections involving the bladder, the prostate, and the urethra. In other embodiments, the drug delivery device is used to treat fibrosis of a genitourinary site, such as the bladder or uterus. Drugs suitable for use in the implantable drug delivery devices described herein are known in the art and/or are described in the patent applications that are cited above and incorporated herein by reference.

Publications cited herein and the materials for which they are cited are specifically incorporated herein by reference. Modifications and variations of the methods and devices described herein that are obvious to those skilled in the art from the foregoing detailed description are intended to come within the scope of the appended claims.

We claim:

1. A drug delivery device comprising:
    a drug reservoir which is loaded with a drug for controlled release and which has two opposed ends; and
    a retention structure operably associated with the drug reservoir, the retention structure comprising a two-part fastening or locking device having each of its two parts positioned respectively at each of the opposed ends of the drug reservoir,
    wherein the two-parts are configured to be connected together to maintain the drug delivery device in a retention shape.

2. The drug delivery device of claim 1, wherein the two-part fastening or locking device comprises two magnets.

3. The drug delivery device of claim 1, wherein the two-part fastening or locking device comprises a hook and an eye loop.

4. The drug delivery device of claim 1, wherein the two-part fastening or locking device comprises a screw and a threaded opening.

5. The drug delivery device of claim 1, wherein the retention shape is relatively circular.

6. The drug delivery device of claim 1, wherein the drug reservoir comprises an elongated tube that can be deformed between a relatively linear deployment shape and a relatively circular retention shape.

7. The drug delivery device of claim 1, wherein the drug is a solid or semi-solid form.

8. The drug delivery device of claim 1, which is configured for deployment into the bladder of a human patient through the patient's urethra.

9. A method of administering a drug to a patient in need thereof, comprising:
deploying the implantable drug delivery device of claim 1 into the patient; and
releasing from the deployed device the drug into the patient.

10. The method of claim 9, wherein the step of deploying the implantable drug delivery device comprises deploying the device through a deployment instrument into the patient's bladder.

11. A drug delivery device comprising:
a drug reservoir which comprises a hollow tube which houses a drug, which is in a solid form, the hollow tube having two opposed ends and being configured to provide controlled release of the drug; and
a retention structure operably associated with the drug reservoir, the retention structure comprising a two-part fastening or locking device having each of its two parts positioned respectively at each of the opposed ends of the drug reservoir,
wherein the drug delivery device is configured for deployment into the bladder of a human patient through the patient's urethra and the two-parts are configured to be connected together to maintain the drug delivery device in a bladder retention shape.

12. The drug delivery device of claim 11, wherein the two-part fastening or locking device comprises two magnets.

13. The drug delivery device of claim 11, wherein the two-part fastening or locking device comprises a hook and an eye loop.

14. The drug delivery device of claim 11, wherein the two-part fastening or locking device comprises a screw and a threaded opening.

15. The drug delivery device of claim 11, wherein the elongated tube can be deformed between a relatively linear deployment shape and a relatively circular retention shape.

16. The drug delivery device of claim 11, wherein the drug is in the form of solid tablets.

* * * * *